United States Patent
Amling et al.

(10) Patent No.: US 11,202,126 B2
(45) Date of Patent: *Dec. 14, 2021

(54) SIMULTANEOUS DISPLAY OF TWO OR MORE DIFFERENT SEQUENTIALLY PROCESSED IMAGES

(71) Applicant: KARL STORZ Imaging, Inc., Goleta, CA (US)

(72) Inventors: Marc R. Amling, Santa Barbara, CA (US); Helga Schemm, Tuttlingen (DE)

(73) Assignee: KARL STORZ Imaging, Inc., Goleta, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/778,601

(22) Filed: Jan. 31, 2020

(65) Prior Publication Data

US 2020/0169686 A1    May 28, 2020

Related U.S. Application Data

(63) Continuation of application No. 15/902,238, filed on Feb. 22, 2018, now Pat. No. 10,587,836, which is a continuation of application No. 15/000,447, filed on Jan. 19, 2016, now Pat. No. 9,948,881, which is a
(Continued)

(51) Int. Cl.
| | |
|---|---|
| *H04N 21/47* | (2011.01) |
| *H04N 5/45* | (2011.01) |
| *H04N 5/262* | (2006.01) |
| *A61B 1/00* | (2006.01) |
| *A61B 1/06* | (2006.01) |
| *H04N 21/431* | (2011.01) |

(Continued)

(52) U.S. Cl.
CPC ........... *H04N 21/47* (2013.01); *A61B 1/0005* (2013.01); *A61B 1/00009* (2013.01); *A61B 1/0638* (2013.01); *A61B 5/7425* (2013.01); *H04N 5/2624* (2013.01); *H04N 5/45* (2013.01); *H04N 9/12* (2013.01); *H04N 21/4316* (2013.01)

(58) Field of Classification Search
CPC .......... G06F 3/38; H04N 5/45; H04N 5/2624; H04N 5/44591; A61B 1/2624; A61B 1/00009
USPC ....... 345/7, 8, 30, 44, 59, 82, 156–173, 207, 345/409, 473, 629; 348/36, 51, 68, 74, 348/80, 128, 231, 273, 278, 383, 598; 382/128, 274; 600/160, 382, 437
See application file for complete search history.

(56) References Cited

U.S. PATENT DOCUMENTS

| | | | | |
|---|---|---|---|---|
| 5,101,272 A | * | 3/1992 | Plut | H04N 3/27 348/E3.049 |
| 5,233,416 A | * | 8/1993 | Inoue | A61B 1/0646 348/70 |

(Continued)

*Primary Examiner* — Prabodh M Dharia
(74) *Attorney, Agent, or Firm* — Michael Loi

(57) ABSTRACT

A medical imaging system includes an endoscope and a processor. The endoscope includes a camera that outputs a video signal with a plurality of portions. The processor receives the video signal and processes a first portion of the plurality of portions according to a first processing mode to generate a first processed video signal, processes a second portion of the plurality of portions of the sensor signal according to a second processing mode to generate a second processed video signal, and generates an output video signal using the first processed video signal and the second processed video signal.

20 Claims, 12 Drawing Sheets

Related U.S. Application Data continuation of application No. 14/035,661, filed on Sep. 24, 2013, now Pat. No. 9,270,919.

(51) Int. Cl.
*A61B 5/00* (2006.01)
*H04N 9/12* (2006.01)

(56) References Cited

U.S. PATENT DOCUMENTS

| | | | | |
|---|---|---|---|---|
| 2003/0103212 | A1* | 6/2003 | Westphal | G01B 9/02083 356/479 |
| 2005/0064602 | A1* | 3/2005 | Kaufman | A61B 5/0071 436/164 |
| 2009/0268015 | A1* | 10/2009 | Scott | A61B 90/361 348/51 |
| 2010/0208054 | A1* | 8/2010 | Farr | A61B 1/0676 348/80 |
| 2013/0073775 | A1* | 3/2013 | Wade | H04N 7/181 710/316 |
| 2016/0199148 | A1* | 7/2016 | Maracaja-Neto | A61B 90/39 600/424 |

* cited by examiner

SIMULTANEOUS DISPLAY OF TWO OR MORE DIFFERENT SEQUENTIALLY PROCESSED IMAGES

CROSS-REFERENCE TO RELATED APPLICATIONS

This application is a continuation of U.S. patent application Ser. No. 15/902,238, filed 22 May 2018, entitled "Simultaneous Display of Two or More Different Sequentially Processed Images," which is a continuation of U.S. patent application Ser. No. 15/000,447, filed 19 Jan. 2016, entitled "Simultaneous Display of Two or More Different Sequentially Processed Images", which is a continuation of U.S. patent application Ser. No. 14/035,661, filed 24 Sep. 2013, entitled "Simultaneous Display of Two or More Different Sequentially Processed Images", both of which are hereby incorporated by reference.

FIELD OF THE INVENTION

The invention relates to image capture, processing and display devices, and more particularly medical imaging and devices.

BACKGROUND OF THE INVENTION

During medical procedures, endoscopes and other imaging devices are used to perform minimally invasive surgery and diagnostics. These imaging devices typically use a broad band light source to illuminate the tissue inside a cavity so that an image sensor can capture the reflected light and send a signal to a processor for display.

A difficulty with the use of a white light or wide band light source is that hemoglobin absorbs the majority of optical light, and the penetration depth of light is closely related to the absorption spectrum of hemoglobin. In the visible spectrum, hemoglobin shows the highest absorption of blue (~410-440 nm) and green (~530-580 nm) wavelength regions. Therefore, optical information obtained in the blue and green spectral region can discriminate hemoglobin concentration in an optimal way. Due to the short penetration depth of blue light (~1 mm), intermediate penetration depth of green light (~3 mm) and high penetration depth of red light (~5 mm), the tissue structures near the surface are easily identified, but information in the red spectral region cannot be easily obtained due to the high penetration depth.

There are some known imaging systems that are capable of reducing the contribution of the red light region to a displayed image. For example, U.S. Pat. No. 7,420,151 to Fengler et al. discloses a system for performing short wavelength imaging with a broadband illumination source and includes an image processor that receives signals from a color image sensor. The image processor reduces the contribution of red illumination light to an image by computing blue, green, and blue-green (cyan) color components of display pixels from the signals received from the image sensor. The blue, green, and cyan color component values are coupled to inputs of a color monitor for display to produce a false-color image of the tissue.

U.S. Pat. No. 4,742,388 to Cooper et al. discloses a color video endoscope system having a light source and a solid state image sensor that transmits a signal to a video processor that converts the signal from the image sensor into a composite RGB video signal. This RGB signal is received by the video processor and the signal is filtered electronically to vary the color image. Cooper discloses a number of potentiometers that allow the user to select and change red, green and blue gains applied to the signal.

U.S. Pat. No. 6,147,705 to Krauter discloses a video colposcope with a microcomputer having algorithms for color balance. A video camera obtains an electronic image. A CCD sensor converts an image into an analog electrical signal which is amplified and digitized. Using an algorithm-driven digital signal processing circuitry, color saturation, hue and intensity levels of the electronic image are modified according to the DSP reference filter algorithm.

U.S. Pat. No. 7,050,086 to Ozawa discloses a system for displaying a false-color image with reduced red component. The red, green and blue ("RGB") signals are cyclically and sequentially read from a frame memory, and the frames are used to generate a digital video signal for display. The RGB components are emitted from the distal end face of a light guide and these RGB signals are sequentially and cyclically focused on the light receiving surface of a CCD image sensor. These RGB signals are then sequentially used to update a display or display memory. Optionally, the red component may be reduced by a switching circuit to display a false-color image.

Current systems synchronize the display of wide band and narrow band images. When the wide and narrow band images are both displayed on a monitor using a split screen, or on two monitors, the images are updated at the same time. Further, the required resolution for medical imaging devices may be rather high. Fengler appears to disclose that the wide band and narrow band images can be displayed at the same time, but the processor would need sufficient processing speed to accomplish this task.

Cooper appears to disclose a processor including a series of potentiometers that modify the RGB signal in a way that would allow for the elimination of the red component. These potentiometers allow for an adjustable filter that may be set or checked at the beginning of each procedure Ozawa appears to disclose cyclically and sequentially reading image signals. However, wide and narrow band display regions are updated at the same time. Thus if one were to display both wide band and narrow band images on a split screen or two separate monitors, both the wide band and narrow band images would be updated simultaneously.

Improved visualization techniques can be used to provide a system that uses less processing power for the same resolution. Likewise, a higher resolution may be obtained with reduced processing power requirements in comparison to prior art systems.

It is therefore an object of the present invention to provide a system for display of wide and narrow band images that uses a cost effective processing technology.

Yet another object of the present invention is to provide an imaging system that can primarily display information obtained from the blue and green wavelength regions that suppresses the red region while reducing the required processing power in comparison to prior art systems.

It is further an object of the present invention to provide an imaging system with sufficient visibility of wide band and narrow band images with reduced hardware costs.

It is yet another object of the present invention to provide a narrow band imaging system that offers simplified settings for display of narrow band images.

It is yet another object of the present invention to provide a system with enhanced resolution without an increase in processing power.

SUMMARY OF THE INVENTION

These and other objects are achieved by providing a medical imaging system having a processor for receiving a video signal having a plurality of portions. A medical imaging system includes an image sensor that generates a sensor video signal comprising a plurality of portions and a processor configured to receive the sensor video signal and process a first portion of the plurality of portions of the sensor video signal according to a first processing mode to generate a first processed video signal, process a second portion of the plurality of portions of the sensor video signal according to a second processing mode to generate a second processed video signal, and generate an output video signal using the first processed video signal and the second processed video signal.

The processor can alternately update the output video signal using a portion of the first processed video signal followed by a portion of the second processed video signal.

The first portion of the sensor video signal can be processed according to a first spectral bandwidth and the second portion of the sensor video signal is processed according to a different second spectral bandwidth.

A portion of the first processed video signal can be displayed at the same time as a portion of the second processed video signal by transmission of the output video signal to a display.

The medical imaging system can include an interface for communication with the processor for user input to select the first processing mode and the second processing mode.

The plurality of portions can include a plurality of images arranged in a sequence. Each of the plurality of images can include a plurality of color channels. The processor can alternately processes first images of the plurality of images into the first processed video signal and second images of the plurality of images into the second processed video signal. The first images can be processed according to a first spectral bandwidth and the second images can be processed according to a different second spectral bandwidth.

The medical imaging system can include a display that receives the output video signal and displays the first processed video signal in a first display area and the second processed video in a second display area.

In other examples, a medical imaging system includes an endoscope including an image sensor that generates a sensor video signal comprising a plurality of portions, an input module configured to receive the sensor video signal and process a first portion of the plurality of portions of the sensor video signal according to a first processing mode to generate a first processed video signal and process a second portion of the plurality of portions of the sensor video signal according to a second processing mode to generate a second processed video signal, and a control module in communication with the input module and configured to generate an output video signal using a combination of the first processed video signal and the second processed video signal.

The control module can alternately update the output video signal using the first portion of the first processed video signal followed by the second portion of the second processed video signal.

The first portion of the sensor video signal can be processed according to a first spectral bandwidth and the second portion of the sensor video signal is processed according to a different second spectral bandwidth.

A portion of the first processed video signal can be displayed at the same time as a portion of the second processed video signal by transmission of the output video signal to a display.

The medical imaging system can include an interface in communication with the control module for user input to select the first processing mode and the second processing mode.

The plurality of portions can include a plurality of images arranged in a sequence. Each of the plurality of images can include a plurality of color channels. The input module can alternately process first images of the plurality of images into the first processed video signal and second images of the plurality of images into the second processed video signal. The first images can be processed according to a first spectral bandwidth and the second images can be processed according to a different second spectral bandwidth.

The medical imaging system can include a display that receives the output video signal and displays the first processed video signal in a first display area and the second processed video in a second display area.

DETAILED DESCRIPTION OF THE INVENTION

Figure 1A:
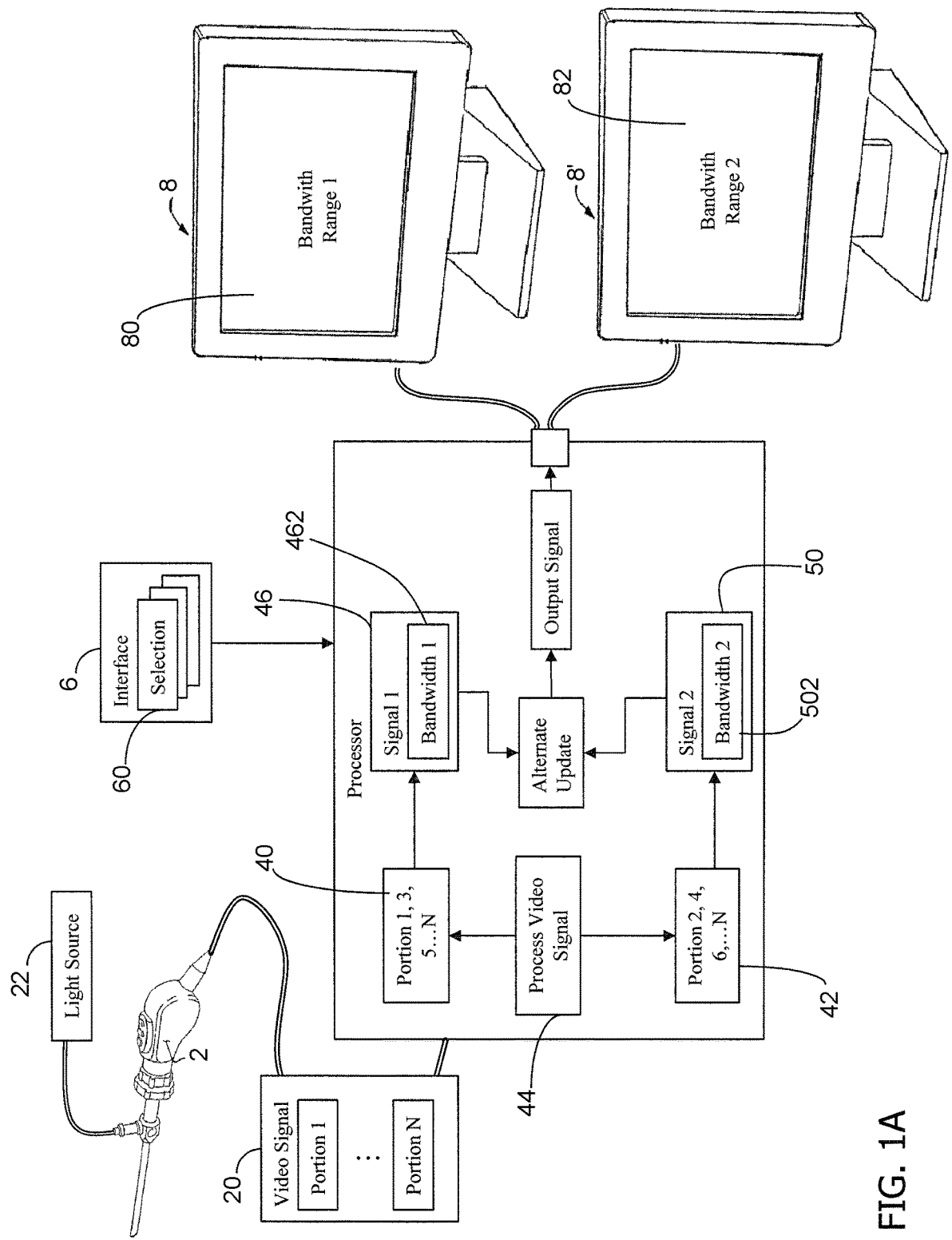
FIG. 1A is a schematic view of the medical imaging system according to an exemplary embodiment.

FIG. 1A shows a medical imaging system having an image capture device or camera, such as an endoscope 2. A light source 22 illuminates the body cavity where the endoscope 2 is inserted. The light source 22 will typically be a broad band or white light source. The endoscope 2 produces a video signal 20, and the video signal has a plurality of portions, etc. The video signal may come to the processor already divided into the plurality of portions. Alternately, the processor 4 can divide the video signal into the portions for processing and display. The processor 4 can exist on a camera control unit or other imaging system. The video signal 20 is processed according to a pattern where different portions of the video signal 20 are processed according to one or more signal processing modes, for example the video signal may be processed according to different bandwidth selections. The selections 60 are received by the processor. These selections 60 can indicate, for example, different signal processing modes such as bandwidth ranges. For example, if it is desirable to reduce or eliminate the red component, a selection of the appropriate bandwidths can be received through an interface 6. The interface may exist on a separate device, such as a computer or wireless device. The interface may also be part of a camera control unit or imaging system having the processor 4.

As shown in FIG. 1A, the selection 60 results in two bandwidth ranges 462, 502 that are used to process the portions of the video signal 20. Each bandwidth range 462, 502 of the video signal forms a signal 46, 50. The signals 46, 50 are alternately updated 48 for display on monitors 8 and 8' having display areas 80, 82.

Figure 1B:
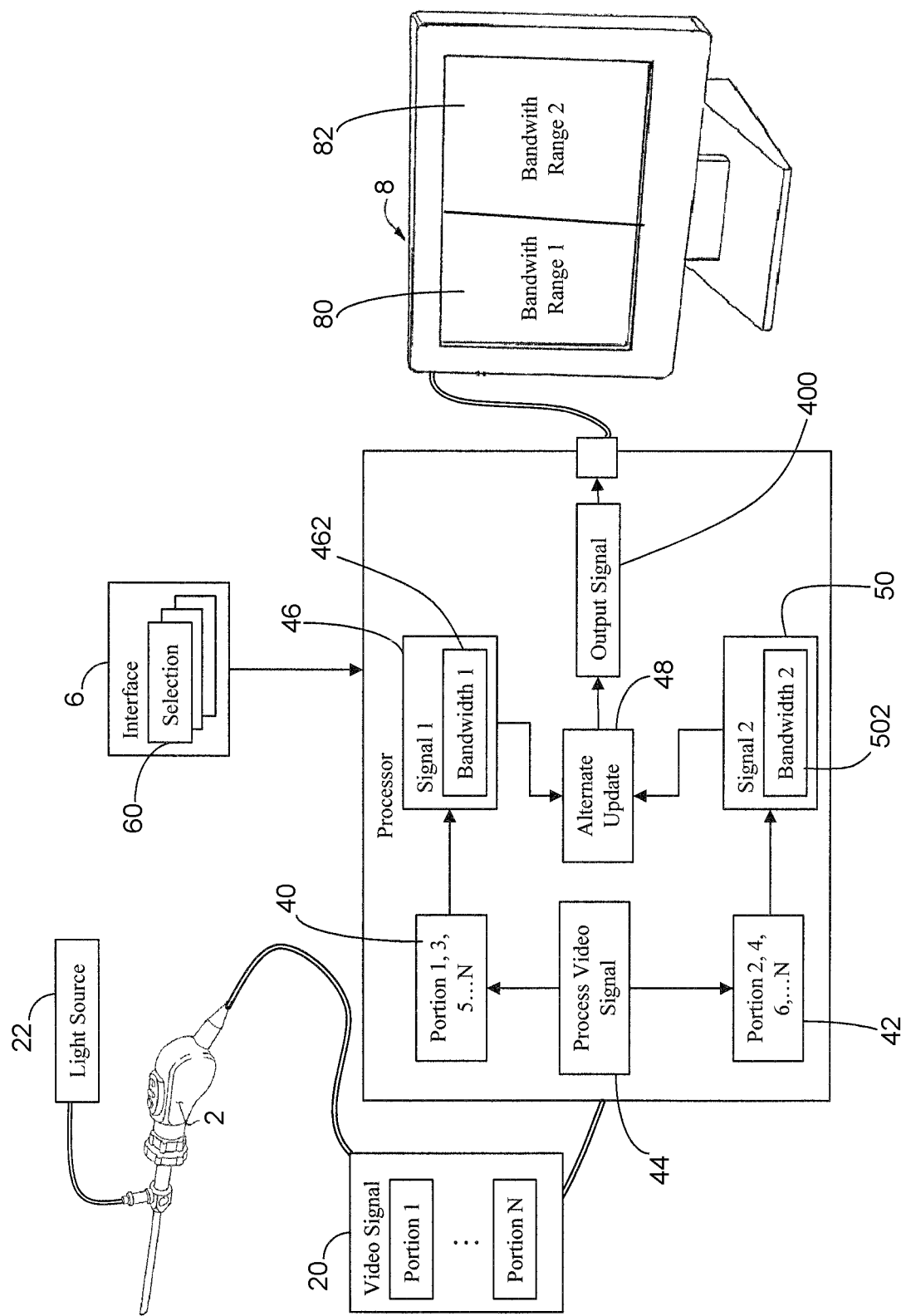
FIG. 1B is another schematic view of another exemplary embodiment of the system of FIG. 1A.

FIG. 1B shows one aspect where the signals 46, 50 are displayed on a single monitor 8 having two display areas 80, 82. Also shown, signals 46 and 50 are combined to form an output video signal 400 for display on the monitor 8.

Figure 1C:
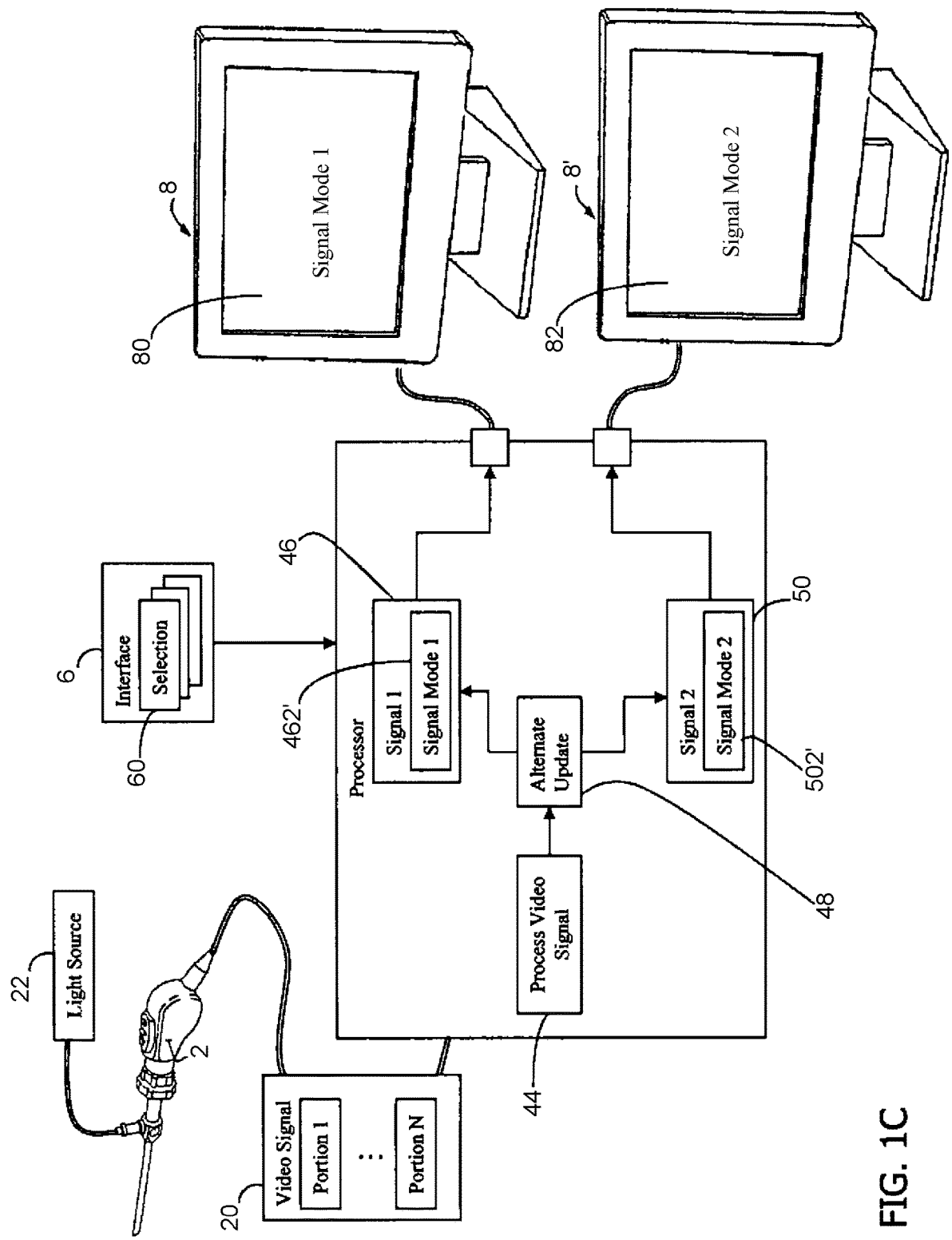
FIG. 1C is another schematic view of another exemplary embodiment of the system of FIG. 1A.
Figure 1D:
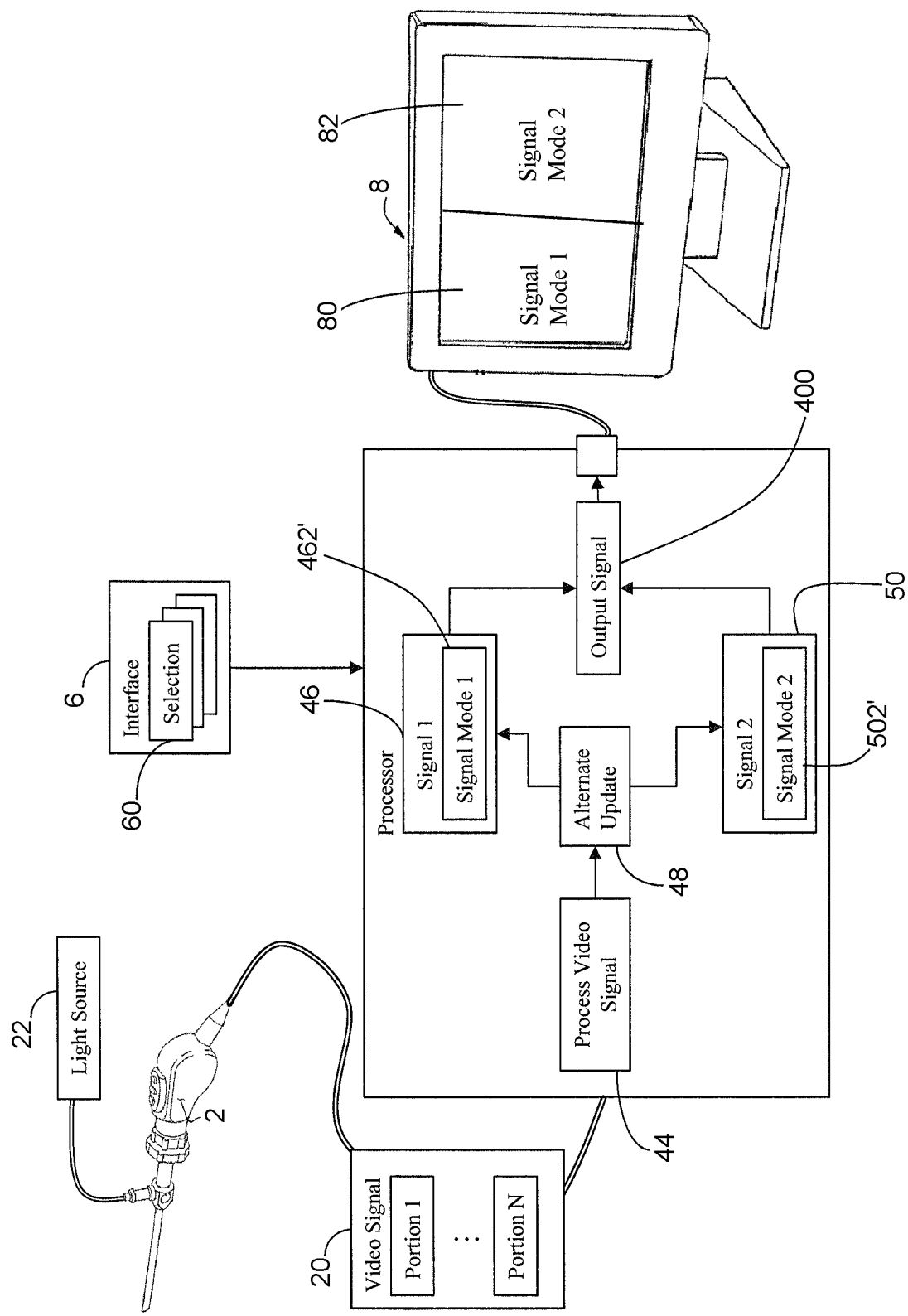
FIG. 1D is another schematic view of another exemplary embodiment of the system of FIG. 1A.

FIG. 1C shows another aspect of FIG. 1A where each signal 46, 50 is processed according to a signal mode 462' and 502'. FIG. 1D shows another aspect of FIG. 1B where each signal 46, 50 is processed according to a signal mode 462' and 502'. It is contemplated that the signal mode can include many different image modification, formatting, filtering and processing techniques. These signal modes will modify the incoming signal, for example, to enhance those aspects or structures that are important to be able to see during a procedure. Optionally, aspects or structures that are less important to see during a procedure are suppressed. Some signal processing modes include a bandwidth selection as shown in FIGS. 1A and 1B. Other signal processing modes may include, for example, edge enhancement, image sharpening or others. Combinations of signal modes are contemplated. For example, a bandwidth mode for signal 46 and an edge enhancement mode may be used for signal 50. Other combinations and permutations are contemplated.

Figure 2A:
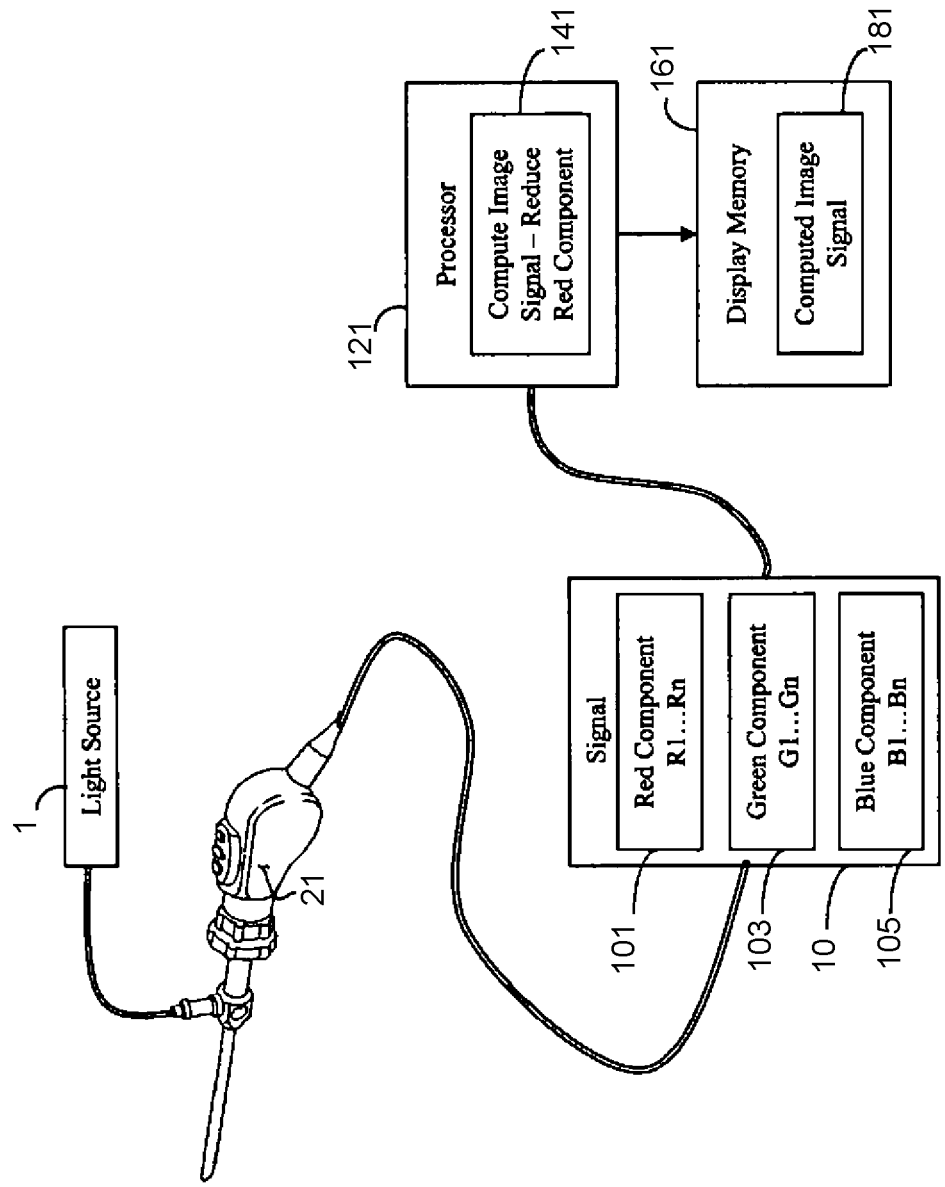
FIGS. 2A and 2B are schematic views of prior art medical imaging systems.

FIG. 2A shows a prior art imaging system with an endoscope 21 having a light source 1. A signal 10 produced by the endoscope 21 includes red 101, green 103 and blue 105 components. A processor 121 computes the signal 10 to reduce the red component 141. This computed image signal 181 is sent to a display memory 161.

Figure 2B:
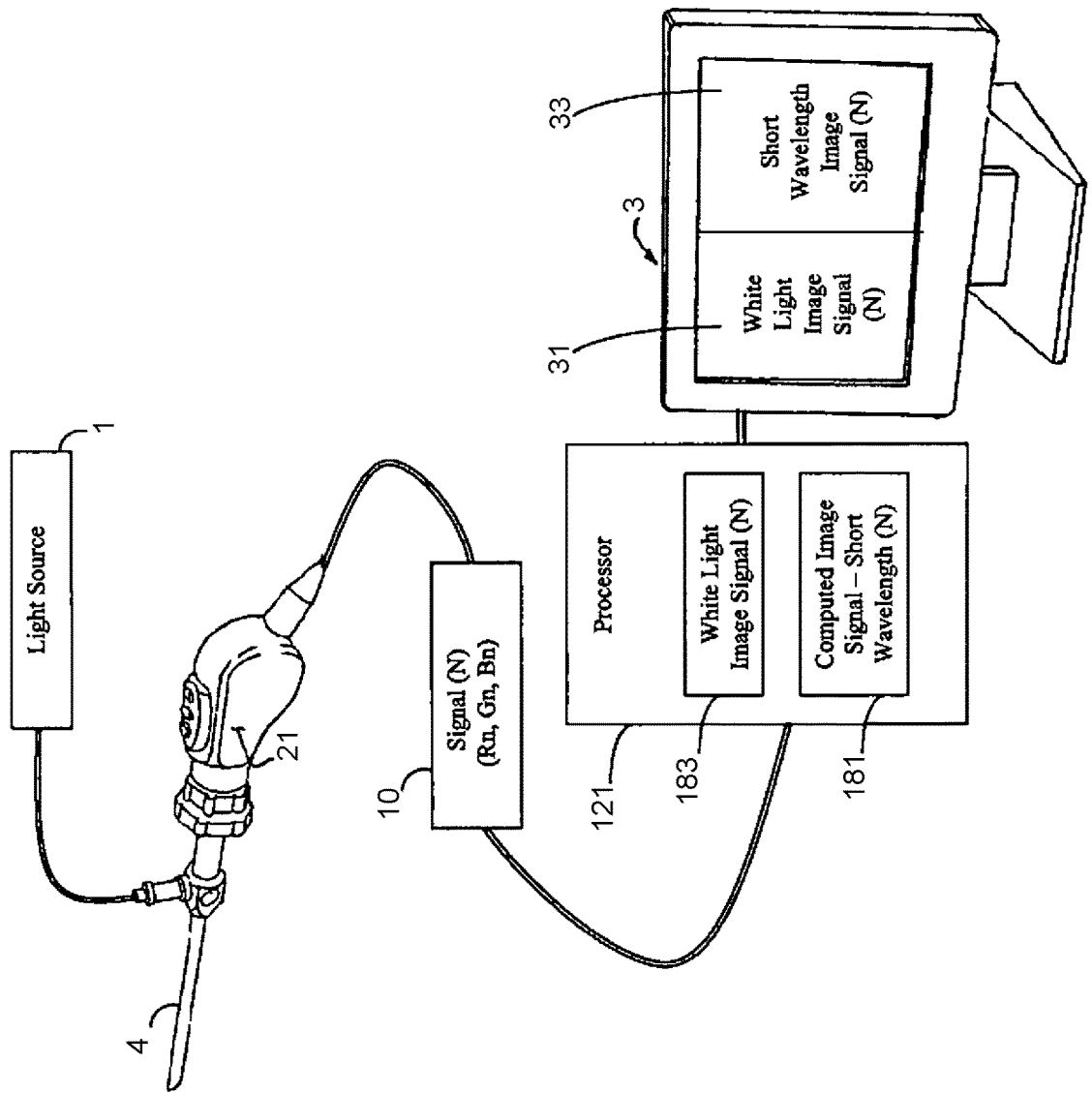

FIG. 2B shows another prior art imaging system with an endoscope 21 having a light source 1. A signal 10 produced by the endoscope 21 includes red, green and blue components. A processor 121 creates a white light image signal 183 and a computed image signal 181. The signals 183 and 181 are sent to a display 3, with two display areas 31, 33. As shown in the figures, the white light image signal 183 and the computed image signal 181 are both produced from the same part of the image signal.

Figure 3A:
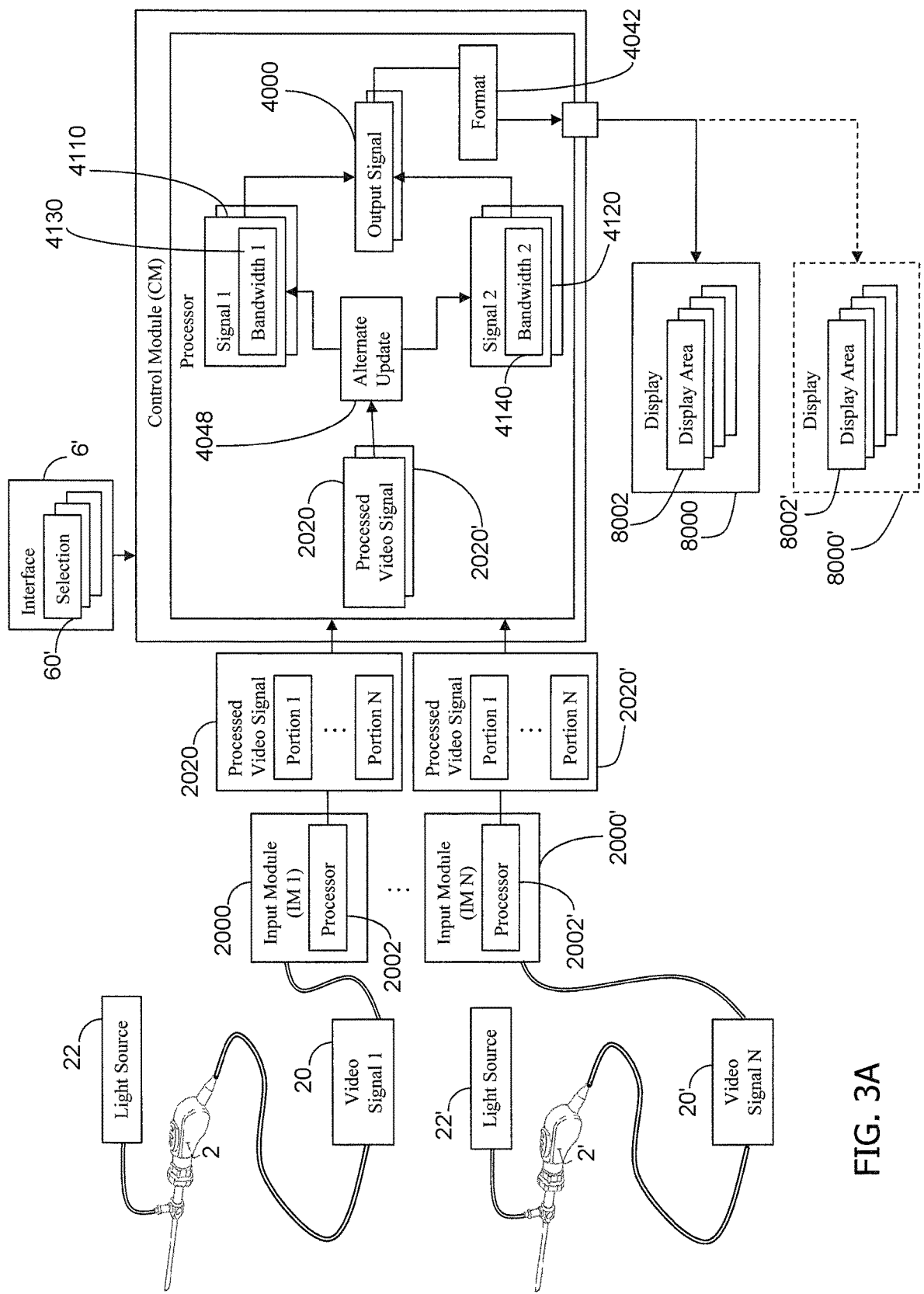
FIGS. 3A-3D are yet other schematic views of a medical imaging system of FIG. 1A according to another exemplary embodiment.

FIG. 3A shows another embodiment of the imaging system of the present invention. In this case, multiple image capture devices, such as endoscopes 2, 2' are each connected to an input module 2000, 2000'. The input modules each have a processor 2002, 2002'. Each input module receives a video signal 20, 20' from the endoscope. The input module processes the video signal 20, 20' to create a processed video signal 2020, 2020'. The control module receives the processed video signals and generates an output video signal 4000, which is formatted 4042 for display. Additional processing can take place after the alternate updating or after the generation of the output video signal. The formatting 4042 can prepare the signal(s) for the appropriate display, for example DVI, VGA, S-Video, Composite, 3G-SDI. In some areas, digital video formats and standards are currently being developed and adopted. The Society of Motion Picture and Television Engineers (SMPTE) is typically in the business of defining and adopting voluminous digital video formal standards. As each is adopted, various applications and application improvements generally will also be realized. Some digital video standards currently in use are: IEEE-1394 FireWire®, ISO/IEC IS 13818, International Standard (1994), MPEG-2, and ITU-R BT.601-4 (1994) Encoding Parameters of Digital Television for Studios.

Figure 3B:
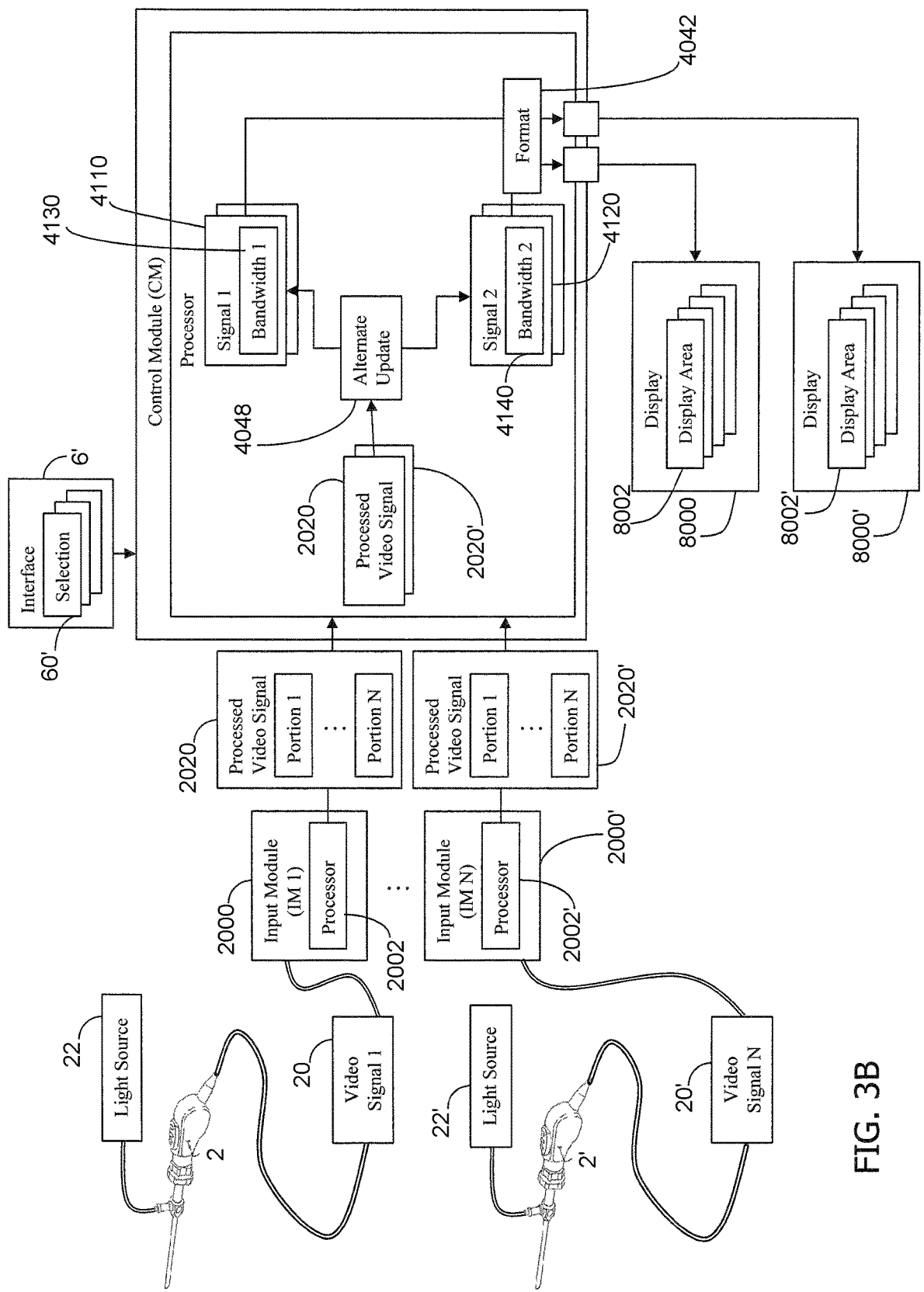

FIG. 3B shows another aspect of the imaging system of the present invention that is similar to FIG. 3A. In this case, the two signals 4110 and 4120 are not combined into a single output signal and the signals 4110 and 4120 are separately sent to displays 8000, 8000'. It should be understood that various combinations of combined or un-combined signals are possible, for example, a video signal 20 may be processed into two signals that are combined to an output video signal, and video signal 20' may be processed into two signals that are not combined and are displayed on separate monitors.

Figure 3C:
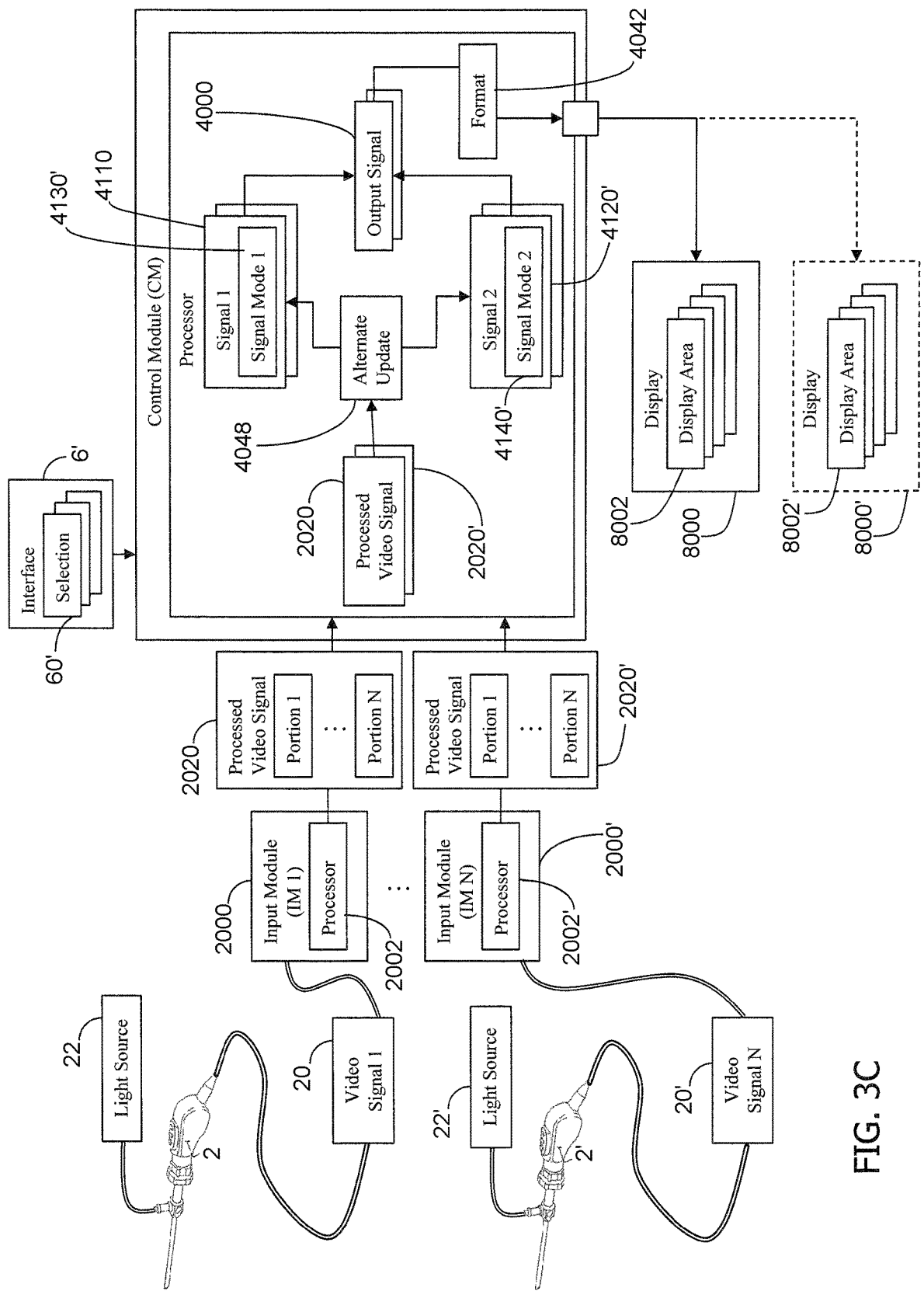
Figure 3D:
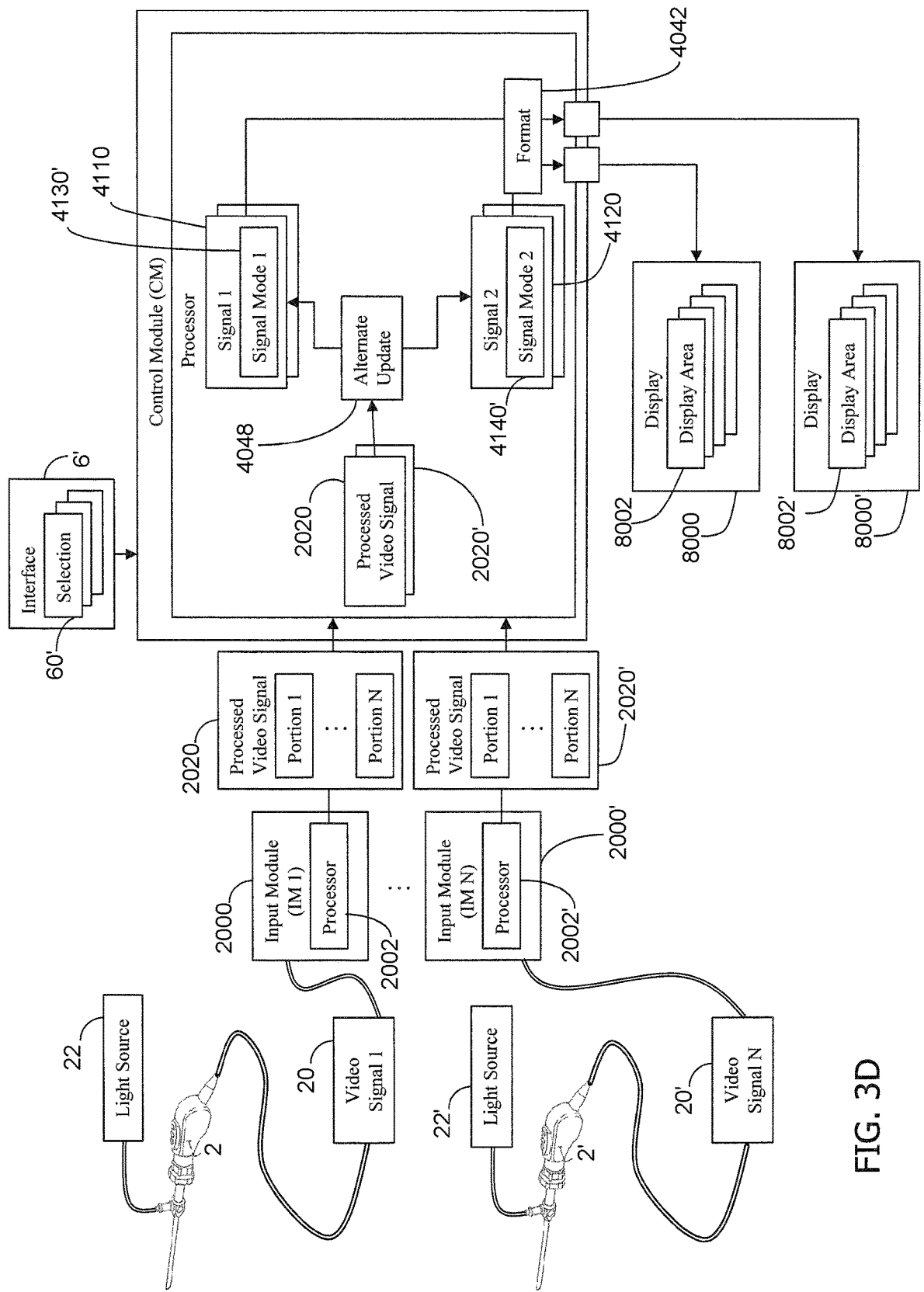

FIGS. 3C and 3D show other aspects where signal modes 4130' and 4140' are used to generate the signals 4110 and 4120. As previously discussed, the signal modes may be bandwidth selections, for example. Other signal modes as discussed herein are contemplated.

The control module can format 4042 the signals and/or the output video signal for display. As shown in FIGS. 3A and 3B, the two signals 4110 and 4120 are generated from different portions of each of the processed video signals 2020, 2020'. Each of the two signals 4110, 4120 is processed according to a bandwidth 4130, 4140. FIGS. 3C and 3D show a similar system where the two signals are processed according to a signal processing mode 4130', 4140'. The output video signal 4000 is alternately updated 4048 with the two signals 4110, 4120 so that the display areas 8002 display different portions of the processed video signal 2020. Other embodiments can include more than two signals, where each signal is processed according to a bandwidth and each of the signals is updated according to an order. For example, if there are three signals, the update order could be update signal 1, update signal 2, update signal 3, repeat. Other orders are envisioned and this example should not be seen as limiting. However, in many cases each of the updates is taken from a different portion of the processed video signal. The example of the order can apply to an imaging system that does not use an input and control module configuration, similar to the system shown in FIG. 1A.

The bandwidths 4130 and 4140 can be selected through an interface 6' that can receive multiple selections 60'. Signal processing modes 4130' and 4140' can also be selected through the interface 6'. The selections 60' may indicate the bandwidth selections or the processing mode selection for processing and display, and these selections are received by the processor. Although two bandwidths 4130, 4140 are shown in FIGS. 3A and 3B, more than two bandwidths may be selected. The same is true for the two signal processing modes 4130' and 4140' shown in FIGS. 3C and 3D. The interface 6' can also select different numbers of bandwidths or signal processing modes for each camera. As an example, the video signal 20 from endoscope 2 can be displayed in two display areas each with a different bandwidth, and the video signal 20' of endoscope 2' can be displayed in four display areas, each with a different bandwidth. Therefore, the interface is configured to allow selections specific to each endoscope. The interface can be configured to have a number of pre-set filter characteristics that adjust the red, green and/or blue components of the video signal. There is also an option for customized settings that would allow settings to be adjusted depending on the specific needs of the physician. For example, customized filter settings. The interface may also be arranged to allow modification to filter characteristics or signal processing modes during a medical procedure to modify the resulting image in a customized way.

In the case of two cameras and two bandwidth selections, there would be four display areas used. The system can combine all four components generated from the video signals for display on a single monitor. Alternately, each camera can be associated with a particular monitor, with each monitor displaying the selected components or signals.

Each of FIGS. 1A-D and 3A-D show an imaging system that generates two signals or components for each camera, each with a different bandwidth. It may be desirable to generate more than two signals or components for each camera. In this case, the interface 6 would receive more than two selections 60. The system may also be programmed with multiple signal processing modes and more than two filter or bandwidth ranges. Each selection would indicate a particular bandwidth or range of bandwidths for use in generating a signal or component of an output video signal. Each signal or component would be generated from a different portion of the video signal or processed video signal, and each signal or component would be associated with a display area. The interface may be, for example, a touch screen, computer interface, buttons, switches, knobs, software or other mechanical, electrical and digital systems that may allow for human interaction with the system to set the parameters of the signal processing mode. It is also understood that a single signal processing mode may be selected for the one of the signals (or components thereof) where the other signal (or component thereof) is processed without modifying the content of the displayed signal. For example, when a bandwidth selection is received, the color components are modified to reduce or enhance a particular color or colors. If not processed according to a signal processing mode in the example of one signal being in false color mode, the other signal could be displayed with no color modification. Similar scenarios are contemplated with other processing modes discussed herein.

It is contemplated that mixtures of combined and uncombined signals can be displayed. For example endoscope 2 can have two signals generated, each with a bandwidth or signal processing mode. The signals of endoscope 2 are then combined for display on a single monitor having two areas. Endoscope 2' can have two signals generated, each with a bandwidth. The two signals can then be displayed on two separate monitors. Thus in the present example, there would be 3 monitors for a total of 4 display areas. Other combinations are contemplated.

Figure 4:
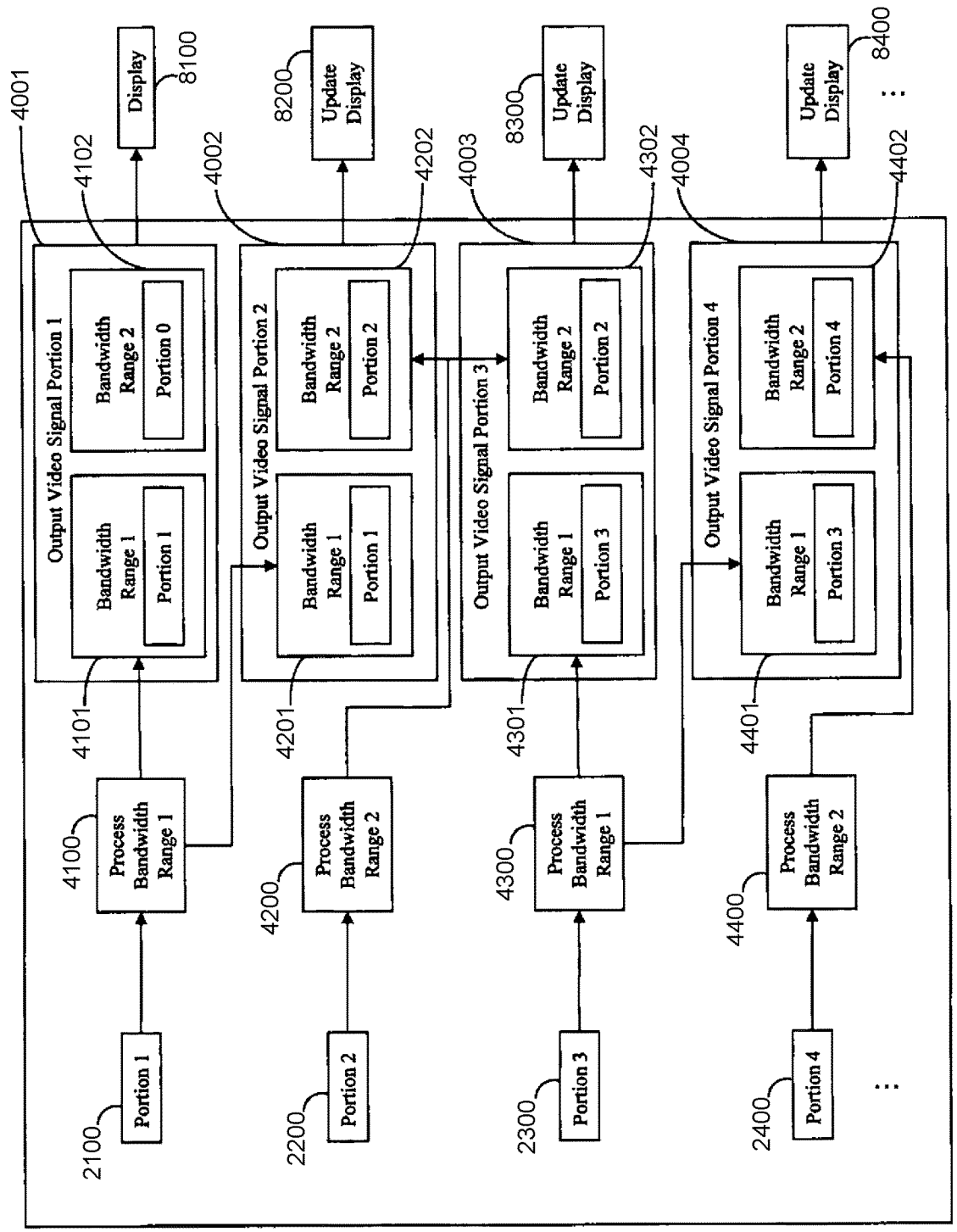
FIG. 4 is a schematic view of an exemplary embodiment of the output signal generation shown in FIGS. 1B, 1D and 3A, 3C.

FIG. 4 shows an example of an output video signal having two components alternately updated for display where the signal processing mode is a false-color image having a bandwidth selection. The first portion of the video signal 2100 is processed according to a first bandwidth range 4100, to generate a first component 4101 of a first portion of the output video signal 4001. The second component 4102 of the first portion of the output video signal 4001 as shown is generated from portion 0. Since portion 0 may not contain data, the first portion of the output video signal 4001 may only have one of the display areas showing content. As shown, the first portion of the output video signal 4001 is displayed 8100 on a monitor.

The second portion 2200 of the video signal is received by the processor and this portion 2200 is processed according to a second bandwidth range 4200 to generate the second component 4202 of the second portion of the output video signal 4002. The first component 4201 of the second portion of the output video signal 4002 is retained from the first portion of the output video signal 4001. That is, component 4101 and 4201 display the same content, and both are generated from the first portion 2100 of the video signal. The second portion 2200 of the output video signal is used to update the display 8200.

The third portion 2300 of the video signal is processed according to the first bandwidth range 4300, the third portion of the output video signal 4003 includes the component 4301, which is generated from portion 2300. The second component 4302 of the third portion of the output video signal 4003 is the same as component 4202, and again, components 4302 and 4301 are generated from different portions of the video signal. The third portion 2300 of the output video signal is used to update the display 8300.

The fourth portion of the video signal 2400 is received by the processor and processed according to the second bandwidth range to generate the second component 4402 of the fourth portion of the output video signal 4004. The first component 4401 of the fourth component of the output video signal 4004 is the same as the first component 4301 of the third portion of the output video signal 4003. The fourth portion of the output video signal 4004 is used to update the display 8400. The process is repeated with each successive portion of the video signal being alternately processed according to the first or second bandwidth range. The previously processed portion is retained for the non-updated component. Therefore, if the portions 2100, 2200, 2300 and 2400 are received at 60 Hz, each component of the output video signal is updated at 30 Hz. Likewise, if there are three bandwidth selections, the portions are received at 60 Hz, and each of the three components of the output video signal is updated at 20 Hz.

Although FIG. 4 shows that the components are generated according to bandwidth ranges, it would be understood by one of skill in the art that the bandwidth ranges shown in the figures can be replaced with other signal modes. For example, the first and/or second components could be generated according to an edge enhancement signal processing mode and the second component can be generated according to a first bandwidth range. The system would alternately update the signal as referenced above, but with the different processing modes. The processing modes may be pre-set in some cases, and in others, the system can receive a selection of processing modes and characteristics of the processing modes. In the case of a false-color processing mode, the selection could first indicate a false-color mode and secondly indicate a particular bandwidth or selection of bandwidth ranges for use with the false-color mode.

Figure 5:
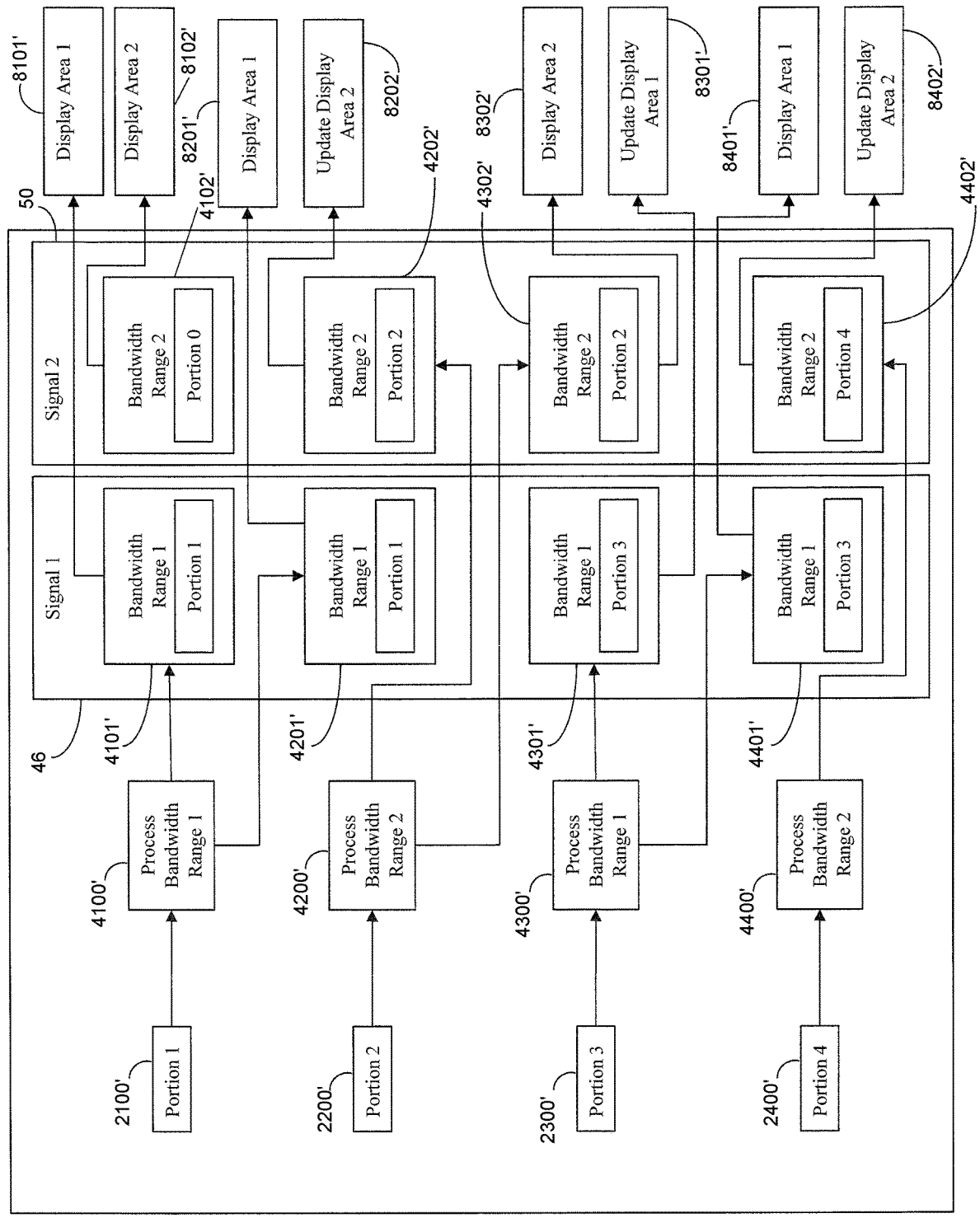
FIG. 5 is a schematic view of an exemplary embodiment of the generation of two signals as shown in FIGS. 1A, 1C and 3B, 3D.

FIG. 5 shows an example of two signals alternately updated for display. The first portion of the video signal 2100' is processed according to a first bandwidth range 4100', to generate a first portion 4101' of the first signal 46. The second portion 4201' of the first signal 46 is retained from the first portion 4101' of the first signal 46. The third portion 4301' of the first signal 46 is generated from the third portion 2300' of the video signal and processed according to the first bandwidth range 4300'. The fourth portion 4401' of the first signal 46 is retained from the third portion 4301' of the first signal 46.

The first portion 4102' of the second signal 50 as shown is generated from portion 0. Since portion 0 may not contain data, the first portion of the second signal may only have one of the display areas showing content. The second portion 4202' of the second signal 50 is generated from the second portion 2200' of the video signal and processed according to a second bandwidth range 4200'. The third portion 4302' of the second signal 50 is retained from the second portion 4202' of the second signal 50. The fourth portion 4402' of the second signal 50 is generated from a fourth portion 2400' of the video signal and processed according to the second bandwidth range 4400'.

As shown, the first portions of the respective signals are for display in display areas 8101' and 8102'. The second, third and fourth portions of the respective signals are for updating the display 8202', 8301' and 8402'. The non-updated portion 8201', 8302' and 8401' may be retained from the previously updated portion of the signal. The updating may repeat continuously during display according to the order shown.

Although FIG. 5 shows that the components are generated according to bandwidth ranges, it would be understood by one of skill in the art that the bandwidth ranges shown in the figures can be replaced with other signal modes. For example, the first and/or second signals could be generated according to an edge enhancement signal processing mode and the second component can be generated according to a first bandwidth range. The system would alternately update the signal as referenced above, but with the different processing modes. The processing modes may be pre-set in some cases, and in others the system can receive a selection of processing modes and characteristics of the processing modes. In the case of a false-color processing mode, the selection could first indicate a false-color mode and secondly indicate a particular bandwidth or selection of bandwidth ranges for use with the false-color mode.

The process is repeated with each successive portion of the video signal being alternately processed according to the first or second bandwidth range. The previously processed portion is retained for the non-updated component. Therefore, if the portions 2100', 2200', 2300' and 2400' are received at 60 Hz, the two signals 46', 50' are each updated at 30 Hz. Likewise, if there are three bandwidth selections, the portions are received at 60 Hz, and each of the three signals are updated at 20 Hz. The display updating is continuous according to the order shown, but other orders or patterns are contemplated.

As discussed previously, it is often desirable to process a signal with reduced red component to better visualize tissue structures. The video signal can be processed to reduce or enhance different color components. The system can also be adapted to process a video signal from a CMYG color sensor. In such a case, the relevant color components from the CMYG sensor can be reduced or enhanced depending on the desired filter characteristics.

The present system includes a computed virtual chromoendoscopy (CVC) system that provides for enhanced visibility between certain structures with different hemoglobin concentrations and to enhance visibility of surface structures to distinguish and classify types of tissue.

The present system uses a broadband white-light illumination (light source), and endoscope optics and video sensors, and a Camera Control Unit (CCU) having a processor or a Modular Camera Control Unit having a processor. The control unit is capable of a full color conversion calculation using software-based image processing. A Red-Green-Blue (RGB) color image sensor can be used. The image processor utilizes matrices that transform acquired color channels into a false-color image in order to display relevant tissue features more clearly. The color channels may be, for example, CCD or CMOS. Primarily, blue and green spectral wavelength regions are utilized, while the red spectral wavelength region is suppressed or attenuated. CMYG sensors can also be used to capture the video signal. Likewise, the relevant components from the CMYG sensor can be enhanced, reduced or otherwise modified according to the desired filter.

In the present system, the settings in the color conversion can be chosen so that: a normal white-light image rendering (with natural colors) is obtained, or a false-color image rendering is obtained, in particular, where the signals from the blue and green input channels are essentially used to generate the output image, while the signal from the red color channel is strongly suppressed. The system provides one or more different filter options for obtaining a false-color image. Each filter may produce a different intensity of the false-color scheme for assisting the practitioner in imaging the tissue of interest.

One example of the color transformation coefficient matrices used for the present filter modes are as follows, with the coefficients represented by letters a-i, and SPIE representing the transformed or false-color image:

$$\begin{bmatrix} r \\ g \\ b \end{bmatrix} SPIE = \begin{bmatrix} a & b & c \\ d & e & f \\ g & h & i \end{bmatrix} \times \begin{bmatrix} R \\ G \\ B \end{bmatrix} = \begin{bmatrix} aR & +bG & cB \\ dR & eG & fB \\ gR & hG & iB \end{bmatrix}$$

In one example, the filter coefficients may be as follows:

$$\begin{bmatrix} r \\ g \\ b \end{bmatrix} SPIEs = \begin{bmatrix} -0.0409 & 1.3204 & -0.3128 \\ -0.0409 & 0.1836 & 1.0032 \\ -0.0409 & 0.0324 & 1.0088 \end{bmatrix} \times \begin{bmatrix} R \\ G \\ B \end{bmatrix} =$$

$$\begin{bmatrix} -0.0409R & +1.3204G & -0.3128B \\ -0.0409R & +0.1836G & +1.0032B \\ -0.0409R & +0.0324G & +1.0088B \end{bmatrix}$$

The present system is implemented with matrix multiplication in a color space where luminance and chrominance are combined. In this design, the input color signal is a combined RGB signal. The output is a RGB signal, which may have been color converted to a false-color image rendering. Other filter coefficients are contemplated and the example above should not be seen as limiting.

Although aspects of the present system have been described with reference to a reduced red component, the video signal may be processed for reduced blue, green or other components. In this case, the above example of the filter coefficients, reduced blue or green component would require different filter characteristics. The same holds true for a CMYG sensor or any other type of sensor in that the filter can be selected to modify the image to show desired characteristics.

As discussed previously, many signal processing display modes are contemplated with the present system. The signal processing modes modify the incoming image signal so that a modified image signal can be displayed. Some of these include switching between a normal white-light image or a computed mode image on a singular display; displaying both the normal white-light image and the computed mode image side-by-side on a singular display; a picture-in-picture display featuring both the normal white-light image and the computed mode image; and displaying the normal white-light image and the computed mode image on two separate displays. Further, switching from white-light image rendering to computed mode may not require additional white balance. The system can also update various other types of signal processing modes for display. The types of signal processing modes can include, for example, false or enhanced color, edge enhancement, texture enhancement, sharpness adjustment, and fiber image bundle. The fiber image bundle may remove a honeycomb mosaic resulting from different optical fiber bundles. This list should not be seen as exhaustive as other signal processing modes can be used to modify the incoming signal or portion of a signal for display.

Edge enhancement may include a signal processing technique that recognizes certain tissue structures based on their reaction to the light source. The edge enhancement technique would therefore modify the signal based on a computation that would identify the location of an edge of a particular tissue structure or type of tissue structure. This may help a physician identify the tissue structure.

In the present system, the white light and computed images are processed by alternating portions of the video image. It is also contemplated that different types of computed images may be used where appropriate, and the computed images may be processed according to a signal processing mode. In some cases, it may be desirable to have all displays showing computed images of different types. It is also contemplated that different color enhancements can be used, for example, red, blue and green components can all be attenuated, enhanced or suppressed to create different false-color images. As an example, the first captured portion is processed to display a first white light image. The second captured portion is processed to display a first computed image. The third captured portion is processed to update the white light image. The fourth captured portion is processed to update the computed image, and so on. As discussed above, it is contemplated that the first white light image may be replaced with a second computed image. It is also contemplated that more than two processing modes can be displayed and alternately updated. For example, a first portion is processed to display a first computed image, a second portion processed to display a second computed image, a third portion processed to display a third computed image and a fourth portion processed to display the first computed image, with the pattern repeating as additional portions are processed for display. It is also understood that different bandwidth selections within a false or enhanced color mode can be considered different signal processing modes. For example, a first signal processing mode could be a white light or wide band mode and a second processing mode could be a reduced-red light or narrow band mode. These examples provided are not intended to be limiting as other combinations and updating patterns can be used to display the computed image(s).

What is claimed is:

1. A medical imaging system comprising:
   an endoscope comprising a camera that outputs a single sensor video signal provided by an image sensor, the sensor video signal comprising a plurality of portions; and
   a processor that receives the sensor video signal and processes a first portion of the plurality of portions of the sensor video signal according to a first processing mode to generate a first processed video signal, processes a second portion of the plurality of portions of the sensor video signal according to a second processing mode to generate a second processed video signal, and generates an output video signal using the first processed video signal and the second processed video signal for simultaneous display of the two sequentially processed video signals from the single sensor video signal.

2. The medical imaging system of claim 1, wherein the first processing mode includes white light imaging comprising natural colors.

3. The medical imaging system of claim 2, wherein the second processing mode includes false color imaging comprising color enhancement for at least one of red, green, and blue color components.

4. The medical imaging system of claim 2, wherein the second processing mode includes edge enhancement imaging that recognizes certain tissue structures based on a reaction to light.

5. The medical imaging system of claim 3, wherein the processor alternately updates the output video signal using a portion of the first processed video signal followed by a portion of the second processed video signal.

6. The medical imaging system of claim 4, wherein the processor alternately updates the output video signal using a portion of the first processed video signal followed by a portion of the second processed video signal.

7. The medical imaging system of claim 1 further comprising an interface in communication with the processor for user input to select the first processing mode and the second processing mode.

8. The medical imaging system of claim 1, further comprising a display that receives the output video signal and displays the first processed video signal in a first display area and the second processed video in a second display area.

9. The medical imaging system of claim 1, wherein the plurality of portions includes a plurality of images formed by frames of the video signal.

10. The medical imaging system of claim 1, wherein the first processing mode filters the first portion of the video signal based on a first bandwidth range and the second processing mode filters the second portion of the video signal based on a second bandwidth range.

11. The medical imaging system of claim 10, wherein the first bandwidth range and the second bandwidth range are different.

12. The medical imaging system of claim 10, wherein the first bandwidth range includes a partial bandwidth range of the second bandwidth range.

13. The medical imaging system of claim 12, wherein the partial bandwidth range includes filtering to reduce a red component of the video signal.

14. The medical imaging system of claim 12, wherein the partial bandwidth range includes filtering to reduce a green component of the video signal.

15. The medical imaging system of claim 12, wherein the partial bandwidth range includes filtering to reduce a blue component of the video signal.

16. A medical imaging system comprising:
   an endoscope comprising an image sensor that generates a sensor video signal comprising a plurality of portions; and
   a processor that receives the sensor video signal and processes a first portion of the plurality of portions according to a first processing mode to generate a first processed video signal, processes a second portion of the plurality of portions according to a second processing mode to generate a second processed video signal, and generates an output video signal using the first processed video signal and the second processed video signal, wherein the processor alternately updates the output video signal using a portion of the first processed video signal and a portion of the second processed video signal.

17. The medical imaging system of claim 16, wherein the first processing mode includes white light imaging comprising natural colors.

18. The medical imaging system of claim 17, wherein the second processing mode includes false color imaging comprising color enhancement for at least one of red, green, and blue color components.

19. The medical imaging system of claim 16, further comprising a display that receives the output video signal and displays the first processed video signal in a first display area and the second processed video in a second display area.

20. The medical imaging system of claim 16, wherein the plurality of portions includes a plurality of images formed by frames of the video signal.

* * * * *